United States Patent
Barnes et al.

(10) Patent No.: US 6,924,403 B2
(45) Date of Patent: Aug. 2, 2005

(54) SYNTHESIS OF HEXAFLUOROPROPYLENE

(75) Inventors: John James Barnes, Hockessin, DE (US); Kenneth Paul Kelch, Washington, WV (US); Thomas D. Sandbrook, Mineral Wells, WV (US); David John Van Bramer, Belpre, OH (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 101 days.

(21) Appl. No.: 10/431,407

(22) Filed: May 7, 2003

(65) Prior Publication Data

US 2004/0002621 A1 Jan. 1, 2004

Related U.S. Application Data

(60) Provisional application No. 60/391,915, filed on Jun. 26, 2002.

(51) Int. Cl.[7] ...................... C07C 17/25; C07C 17/093; C07C 17/26; C07C 17/35; C07C 17/37
(52) U.S. Cl. ...................... 570/172; 570/171; 570/175; 570/240
(58) Field of Search ................................ 570/171, 172, 570/175; 422/240

(56) References Cited

U.S. PATENT DOCUMENTS

| | | | |
|---|---|---|---|
| 2,394,581 A | 2/1946 | Benning et al. |
| RE23,425 E | 10/1951 | Harmon |
| 2,758,138 A | 8/1956 | Nelson |
| 2,970,176 A | 1/1961 | Ten Eyck et al. |
| 3,306,940 A | 2/1967 | Halliwell |
| 3,446,858 A | 5/1969 | Shingu et al. |
| 3,873,630 A | 3/1975 | West |
| 5,334,783 A | 8/1994 | Freudenreich et al. |
| 6,013,890 A | 1/2000 | Hulsizer |

OTHER PUBLICATIONS

B. Adkinson et al., "The Thermal Decomposition of Tetrafluoroethylene", Journal of the Chemical Society, 1957, pp. 2086–2094, XP002254872 Chemical Society, Letchworth., GB ISSN: 0368–1769, p. 2086–2087.

"Preparation and Technology of Fluorine and Organic Fluorine Compounds," National Nuclear Energy Series, VII–I Chapter 32 (PP 567–685), 1987.

*Primary Examiner*—Elvis O. Price

(57) ABSTRACT

The present invention relates to the process of pyrolyzing tetrafluoroethylene to hexafluoropropylene by carrying out the pyrolysis in a tubular reactor that is lined with either nickel or nickel alloy which contains no greater than 8 wt % chromium.

11 Claims, No Drawings

SYNTHESIS OF HEXAFLUOROPROPYLENE

BACKGROUND OF THE INVENTION

1. Field of the Invention

The invention relates to the synthesis of hexafluoropropylene from tetrafluoroethylene.

2. Description of Related Art

Hexafluoropropylene (HFP) is a well known fluoromonomer used for copolymerization with other fluoromonomers to form fluoropolymers such as tetrafluoroethylene(TFE)/HFP copolymer commonly know as FEP. The principal method of making HFP is by the pyrolysis of TFE. This pyrolysis reaction is disclosed in U.S. Pat. No. 2,758,138 as follows:

$$C_2F_4 \rightarrow 2CF_2$$

$$C_2F_4 + CF_2 \rightarrow C_3F_6 \text{ (HFP)}$$

As disclosed in '138, the pyrolysis reaction is carried out by feeding TFE into a reaction zone described as a reaction tube at a temperature of 750° C. to 900° C. and at certain feed rate, and reduced pressure conditions to obtain yields above 75%. The tubular reactor is made of or lined with alloy steel or other high temperature resistant material which is substantially inert to the reaction products. The Examples use a small stainless steel reaction tube ⅜ in (0.95 cm) in diameter. In an earlier disclosure, W. T. Miller, Jr., "Preparation and Technology of Fluorine and Organic Fluorine Compounds", National Nuclear Energy Series, VII-I, Chapter 32 (pp. 567–685), the pyrolysis of TFE is carried out using a nickel tube, 2.5 cm I.D., and heated along a 12 in (30.5 cm) length to a temperature of 435–750° C. (p. 592). U.S. Pat. No. 2,970,176 discloses the carrying out of the TFE pyrolysis reaction at temperatures of 700° C. to 900° C., but wherein higher boiling perfluoroolefins than TFE are co-fed to the reactor tube. The reactor tube is a ½ in diameter 15 ft long stainless steel pipe arranged in loops (helical coil). These patents are followed by U.S. Pat. No. 3,446,858 which discloses carrying out the same pyrolysis reaction but at atmospheric pressure, optionally in the presence of octafluorocyclobutane, by adding superheated steam to the reaction zone. This patent recognizes that stainless steel is not sufficiently inert to the reaction products and uses a tubular reactor of fused silica 22.5 mm long. Unfortunately, fused silica is not suitable for making a commercial size tubular reactor which typically exceeds 50 ft (15.24 m) in length and has a nominal inner diameter of ¾ in (1.9 cm); such reactors are pipes having a 1.05 in (2.67 cm) OD and an ID of 0.824 in (sch 40) or 0.742 in (sch 80), corresponding to IDs of 2.09 cm and 1.88 cm, respectively. Such a fused silica reactor though suitable for laboratory work is too fragile to be used as a material of construction for long commercial reactors, especially when coiling is desired to minimize plant space occupied by the reactor.

U.S. Pat. No. 3,873,630 discloses pyrolysis of TFE to HFP using $CO_2$ as a co-feed, wherein the tubular reactor is made of Inconel® 600 alloy (nickel-chromium (at least 13 wt %) alloy with a small amount of silicon and possibly iron). Inconel® 600 alloy has become the choice for material of construction of the tubular reactor in the TFE pyrolysis reaction because it is relatively inert under the pyrolysis reaction conditions when operated at temperatures no greater than 825° C. Beside being inert, fabricated tubes of the alloy can be welded end-to-end and are ductile so that they can be coiled to form commercial size reactors.

It has been found that operating the Inconel® 600 alloy reactor at temperatures higher than 825° C., e.g. at 830° C., greatly reduces the amount of time that the pyrolysis reaction can be conducted, before the reactor has to be shut down for repair. At the higher operating (pyrolysis) temperature, cracks appear in the wall of the reactor, extending through the entire thickness of the reactor wall. The formation of these cracks occur during the operation of the reactor, sometimes coinciding with an operation incident that causes a sudden increase in stress imposed upon the reactor, as occurs with a sudden change in reactant feed to the reactor, a sudden change in temperature, and/or a mechanical disturbance caused by a shifting of the reactor. This formation of one or more cracks in the reactor wall enables reaction products to escape from the side of the reactor, rather than from the exit end of the reactor for separation and recovery of the HFP, unreacted TFE, and treatment of undesired reaction products, such as perfluoroisobutylene, $(CF_3)_2C=CF_2$ (PFIB), which is toxic. Operation of the reactor at a temperature no higher than 825° C., while providing long HFP production runs between reactor shutdowns, has the disadvantage of a loss in productivity, i.e. less HFP is produced by the reactor.

BRIEF SUMMARY OF THE INVENTION

The present invention involves first the discovery of the unobvious source of the problem (cracks forming in the wall of the Inconel® 600 alloy tubular reactor) and then the solution to the problem.

Acids, such as HCl or HF, or corrosive fluorine ($F_2$) gas, might be suspected as being responsible for the formation of the cracks in the reactor wall, but these corrosive materials are not present in the reactor under the conditions of the pyrolysis reaction. If the feed to the reactor were to contain hydrogen, either as hydrogen gas or as a component of a feed compound being pyrolyzed, then an acid would be formed in the reaction. For example, if the feed contained or consisted of chlorodifluoromethane, $CF_2HCl$ (FC-22), one mole of HCl could be formed for each mole of $CF_2HCl$ converted to reaction product. The TFE feed in the pyrolysis reaction forming HFP does not contain any hydrogen. As indicated by the TFE→HFP reaction sequence described above, the pyrolysis of TFE decomposes the TFE feed to $CF_2$, and this $CF_2$ adds to TFE to form HFP and a small amount of PFIB by-product, i.e. no H-acid or $F_2$ is formed in the reaction.

Examination of a crack in the Inconel® 600 alloy reactor revealed the failure in the wall resembled brittle failure, which was not to be expected from the ductile alloy. The thickness of the wall at the fracture area was about the same as the original wall thickness.

Photomicrographs (31×) of the cross-section of the reactor wall at the failure site revealed the intergranular microstructure of the alloy coming apart, i.e. the presence of discontinuities in the form of small cracks between alloy grains, instead of these grains having the appearance of a continuous solid mass. Simply stated, the grain boundaries in the microstructure showed separation. These separations had the appearance of small (micro) cracks between alloy grains and were interconnecting to extend through the entire thickness of the wall, leading to the failure of the wall, by cracking. The photomicrographs also revealed the presence of porosity in the alloy microstructure, which was not visible in wall areas removed from the crack. The presence of the micro-cracks and pores in the reactor wall was greater at and near the inner surface of the reactor than at or near the outer surface.

Scanning electron microscopy (400×) of the reactor wall at the failure site revealed the presence of minute white deposits present in the cracks between alloy grains. X-ray (EDXA) analysis of these white deposits revealed that they were rich in chromium relative to the chromium content of the alloy grains.

As part of the present invention, it has been discovered that notwithstanding the fact that neither H-acid (HF) nor $F_2$ is present in the pyrolysis reaction, chromium fluoride is formed within the thickness of the reactor wall, the chromium coming from the chromium content of the Inconel® 600 alloy and the fluorine somehow coming from the pyrolysis reaction even though the carbon-fluorine bonds in the reactant and reaction products are thermally stable at pyrolysis temperatures. This chromium fluoride originates from intergranular corrosion within the microstructure of the alloy, i.e. forming the microcracks described above. It has been further discovered that this chromium fluoride comprises both $CrF_2$ and $CrF_3$. Chromium fluoride, whether $CrF_2$ or $CrF_3$, each have a high melting point, about 900° C. and about 1400° C., respectively, which is generally greater than the pyrolysis temperature. The combination of these chromium compounds, however, forms a low melting eutectic of 831±5° C. Thus, in the Inconel® 600 alloy reactor, if the pyrolysis temperature were to reach the temperature of this eutectic, molten chromium fluoride ($CrF_2/CrF_3$) is formed. The formation of this molten material accelerates the intergranular corrosion (microcracks) within the reactor wall thickness, thereby weakening the structure, which eventually fractures when subjected to sufficient stress. This intergranular corrosion also causes the formation of pores within the wall thickness, which causes a further weakening of the reactor wall.

The present invention solves the reactor corrosion problem by the process of pyrolyzing TFE to HFP in a reaction zone that is lined with mechanically supported (a) nickel or (b) nickel alloy containing up to 8 wt % chromium. By "mechanically supported" is meant that the Ni or Ni alloy is in the form of a lining of a tubular reactor made of heat resistant material such as Inconel® 600 alloy. The Ni lining is preferred because it is more inert to the pyrolysis reaction, since no significant amount of Cr is present in the lining and such lining shields the heat resistant back-up material that supports the lining from the pyrolysis reaction, whereby the inertness requirement for the back-up material (mechanical support for the lining) is less critical. Nevertheless, the nickel alloy (b) is ten times more inert than the Inconel® 600 alloy containing at least 13 wt % chromium. The mechanical support of linings (a) and (b) is required because these materials of construction of the lining have insufficient strength at the elevated temperatures of the pyrolysis reaction. While this lack of strength might be tolerable in a small straight tube laboratory reactor which is operated for only short running times, it is not tolerable in large reactors, especially those which are formed into a helical loop from straight tubes for space reduction and which are subjected to the stresses of thermal and mechanical shock at varying times during their long periods of operation. If a tube of lining (a) or lining (b) can, by itself, be formed from a straight tube into a helical loop without losing integrity (forming cracks), such lining materials cannot be used by themselves in the pyrolysis reaction without losing integrity. The process of the present invention enables the pyrolysis reaction to be conducted at higher temperature than 825° C. for long periods of time, without forming any cracks in the reactor wall, thereby increasing the production of HFP, both from the standpoint of producing more HFP per unit of operating time and avoiding loss of production by reactor shutdown.

U.S. Pat. No. 2,394,581 discloses the use of a nickel tubular reactor 18 in long in the pyrolysis of polytetrafluoroethylene to HFP (misidentified as hexafluorocyclopropane, but later correctly identified in Reissue Pat. 23,425), but the nickel reactor is lined with platinum.

DETAILED DESCRIPTION OF THE INVENTION

The feed to the reaction zone does not include hydrogen, i.e. neither hydrogen nor any compound which contains hydrogen is co-fed to the reaction zone with the TFE feed. The reaction zone is also free of oxygen, because the Ni lining is susceptible to oxidation at the pyrolysis temperatures.

The reaction zone is defined by the inner surface of the lining (a) or (b) of the tubular reactor. The cross-sectional shape of the tube forming the reactor will usually be round (circular), but may be in the form of other annular cross-sections such as elliptical. The size of the reaction zone will be at least the diameter and lengths set forth above for commercial size tubular reactors. Such tubular reactors have a surface (inner) to volume ratio of at least 5 in$^{-1}$ (2 cm$^{-1}$). More particularly, the volume of the reaction zone, i.e. the volume of the tubular reactor, will generally be at least 0.04 m$^3$ and more often at least 0.2 m$^3$, and the tubular reactor can have such a long length, that for space savings, it could be in the form of a helical coil. Typically, such a coil is formed from straight lengths of tube by bending into the coil shape and welding the coiled shapes together end-to-end to form the helix, using Ni or the Ni alloy (b) described above as welding material, to reduce the possibility of the weld being the point of attack by the pyrolysis reaction. The helical tubular reactor of course forms a helical reaction zone (lined with Ni or the Ni alloy).

The mechanical support for the lining (a) or (b), for example, can be a preformed outer tube, in which the lining is formed, an outer tube that is formed simultaneously with the lining, preformed lining and outer support tubes that are interfitted together and then adhered to one another, or a tube which is formed on the outer surface of the preformed tubular lining. The thickness of the lining (a) or (b) will depend on its method of formation. Intimate contact between the lining and the support tube is desired for the most efficient transfer of externally applied heat through the wall thickness of the tubular reactor. For example, the lining can be formed on the inner surface of the mechanical supporting tube, by plating by conventional means. Thicker Ni linings can be formed by coextrusion of the Ni lining and supporting tube. If the intimacy of contact between the lining and supporting tube is less than desired, i.e. the lining and support tube do not move together in the coiling operation, the lining can be welded to the support tube at its ends. Additional methods for achieving this intimate contact are explosive cladding and hydrodynamic expansion. The weld overlay method can also be used, wherein the supporting tube is formed over the outer surface of the pre-formed tube of lining material by welding a continuous ribbon of the support metal to the outer surface of the lining tube as the metal ribbon is wound in abutting relationship around the outer surface of the lining tube, such as disclosed in U.S. Pat. No. 6,013,890. While the linings in abutting tube ends are welded together using lining materials (a) or (b) as the welding material, the support tube is welded end-to-end using material similar to or the same as the material of construction of the support tube. The thickness of the lining is established by an estimate of the corrosion rate, and the thickness of the support material is established by the estimate of strength required to withstand the stresses expected to be experienced by the reactor in installation, operation and repair of the reactor. Generally, the thickness of the lining is at least 0.001 in (0.0025 cm) thick and preferably at least 0.030 in (0.076 cm) thick, and more preferably at least 0.060 in (0.152 cm) thick, and may be as thick as 1 in (2.54 cm) or thicker. The support tube will generally be at least 1/16 in to 1 in (0.16–2.53 cm) in thickness. If the thermowells (housing for thermocouples communicating through the reactor wall thickness to the interior of the reactor) are not made of lining material because of their lack of strength, the material of construction of the thermowell can also be lined with lining material (a) or (b) where exposed to the pyrolysis reaction.

The Ni lining (a) will consist essentially of Ni, i.e. be free of impurities which have any appreciable adverse effect on the life of the lining under the conditions of the operation of the furnace. The Ni lining will not contain more than about 0.1 wt % of any other element, i.e. the Ni is not an alloy. If carbon is present in the Ni, the amount of carbon should be no greater than about 0.02 wt %, otherwise the carbon will render the Ni lining too brittle. Ni is commonly available as Ni 200, Ni 201, and Ni 270, the latter being the most pure. Ni 200 sometimes contains more than 0.02 wt % C and sometimes can be obtained containing no more than 0.02 wt % carbon content. Thus Ni 200 can be used when it contains no greater than about 0.02 wt % carbon. Ni 201 is preferred, however, based on economy and performance. Weight percents disclosed herein are based on the total weight of the lining material (a) or (b) as the case may be.

The Ni alloy lining (b) will contain at least 60 wt % Ni and can contain up to 8 wt % Cr and still provide great improvement over Inconel® alloy containing at least 13 wt % Cr when the reactor is operated at temperatures above 825° C. Thus Haynes® alloy 242 which has the composition Ni/26 wt % Mo/8 wt % Cr can be used. The Ni alloy can contain other elements which together with the Ni permit high temperature reactor operation, i.e. do not appreciably detract from the corrosion resistance of the Ni component of the alloy. Preferably, if Fe is present in the alloy, no more than 6 wt % thereof is present. Typically, the Ni alloy will contain one or more other metals. An example of such other metal is Mo, and up to 30 wt % thereof can be present. Another example of useful Ni alloy is 61 wt % Ni/28 wt % Mo/1 wt % Cr/5.5 wt % Fe/ 2.5 wt % Cu, the balance being small amounts of Mn and Si, available as Hastelloye® B.

A wide variety of support materials for the lining can be used, such as stainless steel and Inconel® alloy, such as Inconel® 600, 601, and 617. The Inconel alloys typically contain 13 to 25 wt % Cr; alloys 600, 601, and 617 contain 16, 22, and 23 wt % Cr, respectively. The method of adhering the lining to the support material will depend on the particular support tube material of construction. The coiling of the lined tube is done by conventional means. The support material should be oxidation resistant at the high temperatures applied to it in order to heat the reaction zone to the desired pyrolysis temperature. The support material also shields the surface of the lining facing the direction from which heat is applied from oxygen and thereby from oxidative degradation.

The tubular reactor is positioned within a housing which is equipped with means for heating the tubular reactor, such as hot gas passing between the outer surface of the coiled reactor and the inner surface of the housing or a radiant heat source positioned within the housing . The combination of the housing and tubular reactor contained within the housing can be considered the pyrolysis furnace.

The inner wall of the tubular reactor, i.e. the surface of the lining defining the reaction zone, will usually be smooth to minimize the pressure drop of gases passing through the reaction zone.

The TFE feed to the tubular reactor and the treatment of the reaction products flowing from the exit end of the reactor, including separation and recovery of unreacted TFE for recycle to the furnace, and HFP, and disposal of undesirable by-products such as PFIB, are done by conventional methods. The process of the present invention is conducted by continuously feeding TFE into one end of the tubular reactor and continuously withdrawing the unreacted TFE and reaction products from the exit end of the reactor, whereby the reaction system within the reactor involves the continuous passage of these gases through the reaction zone.

The process can be operated at a wide variety of temperature, pressure and contact time conditions, which are selected based on the volume of the furnace to produce HFP most economically, including without producing an excessive amount of undesirable by-products. The temperature of the pyrolysis reaction will generally be at least 700° C., and preferably at least 775° C., but no more than 900° C. Above 900° C., fluorine can split off from its carbon bonding to form corrosive fluorine gas, which can attack the Ni lining, depending on the contact time of the gases passing through the tubular reactor. Typically, contact times (residence time within the reactor-reaction zone) will be from 0.1 to 5 seconds. Preferably, however, the pyrolysis reaction is conducted within the range of 775° C. to 850° C., more preferably 825° C. to 845°, and even more preferably at 830° C. to 845° C. Especially, the latter temperature range provides the advantage over the former use of the Inconel® 600 alloy tubular reactor of being able to operate at a higher temperature, thereby increasing productivity of the desired product HFP, while still sufficiently minimizing the formation of the undesired by-product PFIB. Typically, the feed gas to the reactor is at a relatively low temperature, as low as ambient temperature, and such feed gas becomes heated as it traverses the length of the tubular reactor. Thus heating, together with the exothermic nature of the pyrolysis reaction occurring, brings the reaction to within the desired temperature range towards the end of the reactor, with the highest temperature being encountered adjacent to the exit end of the reactor. Although the length of the reactor is heated within the pyrolysis furnace, the temperature of the pyrolysis reaction is conveniently measured by thermocouple positioned in the thermowell at the exit end of the reactor, this being the actual, highest temperature of the reaction. The reaction can be conveniently conducted at atmospheric pressure, but sub- and super-atmospheric pressure can also be used, such as 0.5 to 1.5 atmospheres.

The TFE feed to the furnace can be accompanied by other feed materials which are reactants or inert in the reaction within the tubular furnace. For example, an inert gas such as nitrogen or argon can be co-fed with the TFE to the reactor to either moderate the heat applied to the reactor or add to it. As a co-reactant, other perfluorocarbons may be co-fed with the TFE to the reactor, such as higher boiling perfluoroolefins or compounds of the formula $C_{n+3}F_{2(n+3)}$, such as octafluorocyclobutane. In one embodiment of the present invention, the feed ratio of a mixture of TFE and octafluorocyclobutane to the furnace contains 0.1 to 2.0 parts by weight of the octafluorocyclobutane/part by weight of TFE.

EXAMPLES

A. Basis for Comparison: A tubular reactor in a helical coil having a volume of 0.2 m³ and made of Inconel 600 alloy (76 wt % Ni, 15.5 wt % Cr, 8 wt % Fe, and the balance being Mn, Cu, and Si) is used as the tubular reactor in the pyrolysis of TFE to HFP. The tubular reactor is externally heated, and together with the exothermic TFE to HFP reaction the highest temperature of the pyrolysis reaction is found at the exit end of the tube, via thermocouple in a thermowell at the exit end of the tube, thereby reading the temperature of the inner surface of the tube at the exit end. The residence time of the gases in the reactor (same as the residence time of the unreacted TFE) is about 2.5 sec. After running the pyrolysis reaction continuously for one month at 825° C., the corrosion rate at the exit end of the tube is 0.25 in (0.64 cm) per year. When this procedure is repeated but at a pyrolysis temperature of 830° C. at the exit end of the tube, the corrosion rate increases to 0.95 in (2.41 cm) per year. The depth of the voids represented by the corrosion rate is determined by observation of photomicrographs (31×) of the wall cross-section and measuring the depth of the microcracks along grain boundaries extending from the inner surface of the tube.

B. The Invention: This pyrolysis reaction of A above at 825° C. is repeated using a helical coil of the same size but wherein the coil is made of ⅛ in (0.32 cm) thick Inconel 617 (55 wt % Ni, 22 wt % Cr, 12.5 wt % Co, and 1.2 wt % Al) lined with Ni 200, which contains 0.015 wt % carbon, 0.32 in (0.81 cm) thick. The Inconel 617 mechanical support is formed over the outer surface of a pre-formed tube of Ni 201 by weld overlay. The pyrolysis reaction temperature and residence time are the same. After two months of continuous operation of the reactor, the lining at the exit end of the reactor has the same appearance as when the reaction was begun. No evidence of corrosion is present. No difference in corrosion (lack of corrosion) is found when the pyrolysis reaction is repeated except at the temperature of 835° C. at the exit end of the reactor. The ability to operate the reactor at the higher temperature represents an increase of about 15% in the production rate of HFP by the reaction.

C. Additional Embodiments:

(1) The pyrolysis reaction of A is repeated again at 830° C., but wherein the Inconel 617 coil is lined with Haynes 242 alloy (92 wt % Ni/8 wt % Cr), with the result being a rate of corrosion of 0.1 in (0.25 cm)/year, which is much improved over the use of the reactor tube of Inconel 617 alloy alone. A similar improvement is obtained when the lining is Ni alloy containing 28 wt % Mo and 1.5 wt % Cr in place of the Haynes 242 alloy lining.

(2) The pyrolysis reaction of B is repeated except that the feed to the reactor is 0.35 parts by weight of octafluorocyclobutane/part by weight of TFE fed to the reactor, and after fours months operation at 825° C. there is no evidence of corrosion of the Ni lining of the reactor as determined by by visual inspection. The absence of corrosion is confirmed by ultrasonic thickness measurement, which reveals the thickness of the lining to be unchanged. A weld in the lining is tested for dye absorption to see if any cracks exist. The weld is found to be crack-free.

What is claimed is:

1. Process for pyrolyzing tetrafluoroethylene to hexafluoropropylene, comprising carrying out said pyrolyzing in a reaction zone lined with mechanically supported (a) nickel or (b) nickel alloy containing up to 8 wt % chromium.

2. The process of claim 1 wherein said pyrolyzing is carried out in the absence of hydrogen.

3. The process of claim 1 wherein said pyrolyzing is carried out at a temperature of 700° to 900° C.

4. The process of claim 3 wherein the temperature is 775° C. to 850° C.

5. The process of claim 3 wherein the temperature is 825° C. to 845° C.

6. The process of claim 1 wherein said reaction zone is in the shape of a helix.

7. The process of claim 1 wherein the volume of said reaction zone is at least 0.04 m³.

8. The process of claim 1 wherein the lining of said reaction zone is nickel.

9. The process of claim 1 wherein the temperature is 830° C. to 845° C.

10. The process of claim 1 wherein said nickel (a) contains no greater than 0.02 wt % carbon.

11. The process of claim 1 wherein said pyrolyzing is carried out with octafluorocyclobutane and said tetrafluoroethylene being co-fed to said reaction zone.

* * * * *